(12) United States Patent
Chia et al.

(10) Patent No.: US 8,470,118 B2
(45) Date of Patent: Jun. 25, 2013

(54) LASER PROBE TIP ASSEMBLY

(75) Inventors: Wen-Jui Ray Chia, Sunnyvale, CA (US); Ming Ko, San Jose, CA (US)

(73) Assignee: AMS Research Corporation, Minnetonka, MN (US)

( * ) Notice: Subject to any disclaimer, the term of this patent is extended or adjusted under 35 U.S.C. 154(b) by 39 days.

(21) Appl. No.: 13/326,834

(22) Filed: Dec. 15, 2011

(65) Prior Publication Data

US 2012/0152453 A1 Jun. 21, 2012

Related U.S. Application Data

(60) Provisional application No. 61/424,143, filed on Dec. 17, 2010.

(51) Int. Cl.
*B29C 65/54* (2006.01)
*B32B 37/12* (2006.01)

(52) U.S. Cl.
USPC .................................. 156/275.5; 156/293

(58) Field of Classification Search
USPC .................................. 156/272.2, 275.5, 293
See application file for complete search history.

(56) References Cited

PUBLICATIONS

Takayuki Funatsu et al., "Photochemical Adhesion of Fused Silica Glass Lens by Silicone Oil," Department of Electrical Engineering, Tokai University, vol. 843, 2005, pp. 221-226.

Jun Ma et al., Preliminary Study of Pyrolysis of Polymethylsilsesquioxane by FT-IR and XPS, State Key Laboratory of Polymer Physics & Chemistry, Chinese Academy of Sciences, Beijing, vol. 13, No. 1. pp. 75-78, 2002.
M. Murahara et al., "Heat and high electric insulation resistant protective coating of solar cell and thermoelectric element for offshore solar power generation," SPIE Laser Damage, XLI Annual Symposium on Optical Materials for High Power Lasers, Sep. 21-23, 2009, 2 pages.
Masataka Murahara et al., "Hard protective waterproof coating for high-power laser optical elements," vol. 30, No. 24, Dec. 15, 2005, pp. 3416-3418.
Masataka Murahara et al., "Anti-Reflective and Waterproof Hard Coating for High Power Laser Optical Elements," Entropia Laser Initiative, Tokyo Institute of Technology, 2006 American Institute of Physics, 9 pages.
Masataka Murahara, "Photochemical Coating and Adhesion of Fused Silica Glass by Using Excimer Lamp at Room Temperature", Bulletin of the Ceramic Society of Japan, vol. 41, No. 6 (2006) pp. 440-443.

*Primary Examiner* — Daniel McNally
(74) *Attorney, Agent, or Firm* — Westman, Champlin & Kelly, P.A.

(57) ABSTRACT

In a method of assembling a laser probe tip, an optical fiber comprising an optical fiber core and silica glass cladding surrounding the core is provided. A fiber cap formed of silica glass is also provided. Silicone oil is applied to a surface of the cladding at a distal end of the optical fiber or an interior surface of the fiber cap. The distal end of the optical fiber is inserted into the interior cavity of the fiber cap. The silicone oil is then converted into silica glass, which bonds the fiber cap to the optical fiber.

9 Claims, 6 Drawing Sheets

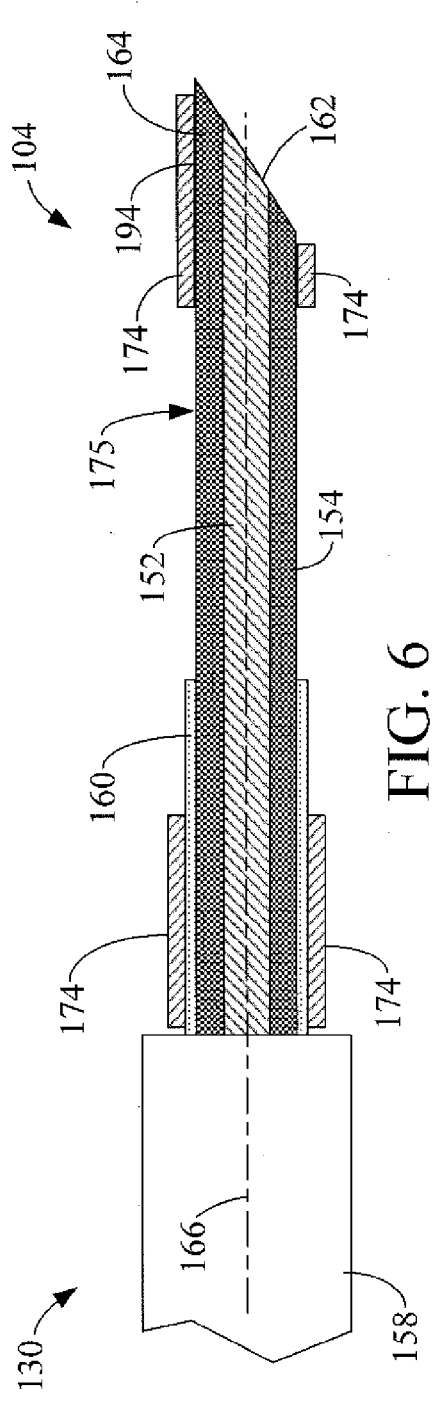
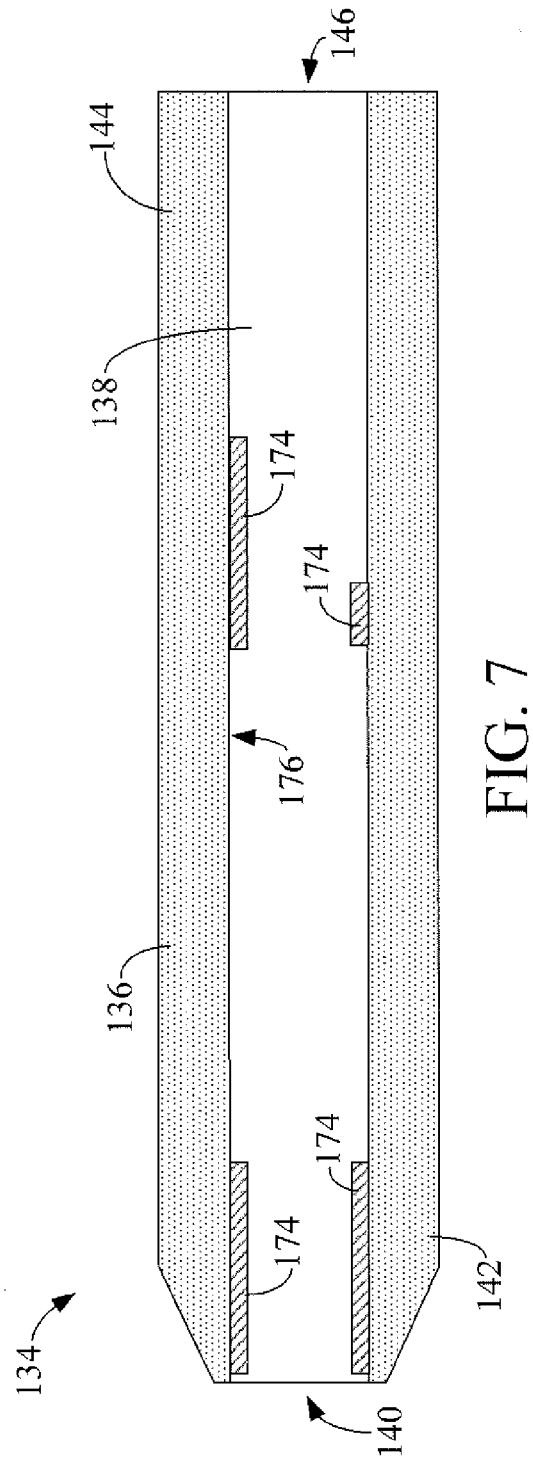
FIG. 6
FIG. 7

LASER PROBE TIP ASSEMBLY

CROSS-REFERENCE TO RELATED APPLICATION

The present application is based on and claims the benefit of U.S. provisional patent application Ser. No. 61/424,143, filed Dec. 17, 2010, the content of which is hereby incorporated by reference in its entirety.

FIELD

Embodiments of the invention are directed to a method of assembling a laser probe tip and, more specifically, to a method of attaching a fiber cap to a distal end of an optical fiber.

BACKGROUND

Medical lasers have been used in various practice areas, such as, for example, urology, neurology, otorhinolaryngology, general anesthetic ophthalmology, dentistry, gastroenterology, cardiology, gynecology, and thoracic and orthopedic procedures. Generally, these procedures require precisely controlled delivery of energy as part of the treatment protocol.

Surgical laser systems utilize a frequency doubled Nd:YAG laser, which operates at 532 nm in a quasi continuous mode at high power levels (e.g., 106 watts) and has been used to efficiently ablate tissue. The frequency doubled Nd:YAG laser can be pumped by CW krypton arc lamps and can produce a constant train of laser light pulses. When ablative power densities are used, a superficial layer of denatured tissue is left behind. At high powers, 532 nm lasers induce a superficial char layer that strongly absorbs the laser light and improves ablation efficiency.

Many surgical laser procedures utilize a surgical probe, which generally comprises an optical fiber and a fiber cap over a distal end of the optical fiber to form a probe tip. A laser source delivers laser energy through the optical fiber to the probe tip where the energy is discharged through the fiber cap and onto desired portions of the targeted tissue.

Laser probe tips are typically assembled by attaching the fiber cap to the distal end of the optical fiber by fusing the glass fiber cap to the inner bare optical fiber after removing the polymer clad. Typically, a $CO_2$ laser is used for this fusion process where the laser beam is focused on a portion of the fiber cap until the portion melts into the outer surface of the bare optical fiber. A thin walled fiber cap is used to assist in facilitating the welding process. This assembly process often leads to low yield due to the difficult fusing process, high costs due to the necessity of a laser station for the welding process, and product reliability concerns due to the thin walled fiber cap that is susceptible to thermal stress.

SUMMARY

Embodiments of the invention are directed to assembly of a probe tip 100 for use in a surgical laser system to discharge electromagnetic radiation. In one embodiment of the method, an optical fiber comprising an optical fiber core and silica glass cladding surrounding the core is provided. A fiber cap formed of silica glass is also provided. The fiber cap comprises a cap body having an interior cavity and an opening to the interior cavity at a proximal end. Silicone oil is applied to a surface of the cladding at a distal end of the optical fiber or an interior surface of the fiber cap. One embodiment of the silicone oil comprises an organosilicone, an organosilicone compound, or a silicone polymer. The distal end of the optical fiber is inserted through the opening and into the interior cavity of the fiber cap, such that the silicone oil engages both the cladding and the fiber cap. The silicone oil is then converted into silica glass. In one embodiment of this conversion process, ultraviolet (UV) radiation is applied to the silicone oil in an atmosphere containing an oxidizing agent. The fiber cap is then bonded to the optical fiber in response to the conversion of the silicone oil into silica glass.

Other features and benefits that characterize embodiments of the present disclosure will be apparent upon reading the following detailed description and review of the associated drawings.

BRIEF DESCRIPTION OF THE DRAWINGS

FIG. 6 is a side cross-sectional view of a distal end of an optical fiber illustrating a method step in accordance with embodiments of the invention.

FIG. 7 is a simplified side cross-sectional view of a fiber cap illustrating a method step in accordance with embodiments of the invention.

DETAILED DESCRIPTION OF ILLUSTRATIVE EMBODIMENTS

Figure 1:
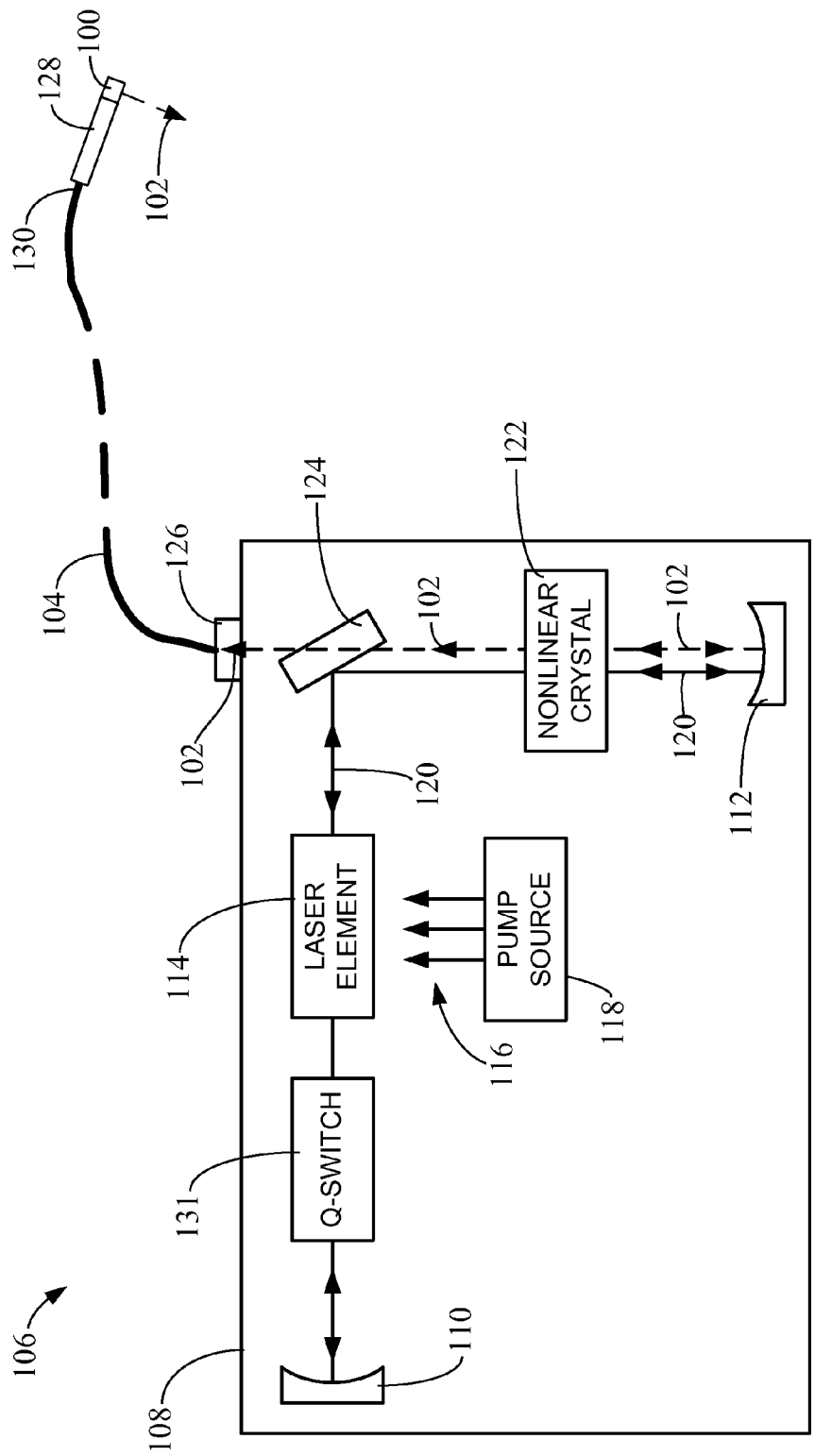
FIG. 1 is a simplified block drawing of an exemplary surgical laser system in accordance with embodiments of the invention.

Embodiments of the invention are directed to the assembly of a probe tip 100 that is configured to discharge electromagnetic radiation 102 from an optical fiber 104, as illustrated in the simplified block diagram of a surgical laser system 106 provided in FIG. 1. The exemplary system 106 comprises a laser resonator 108. The laser resonator 108 may include a first resonator mirror 110, a second resonator mirror 112 and a laser rod or element 114. In one embodiment, the laser element 114 comprises a yttrium-aluminum-garnet crystal rod with neodymium atoms dispersed in the YAG rod to form a Nd:YAG laser element. Other conventional laser elements 114 may also be used.

The laser element 114 is pumped by a light input 116 from an optical pump source 118, such as a Kr arc lamp or other conventional pump source, to produce laser light or beam 120 at a first frequency. The laser resonator 108 also includes a nonlinear crystal 122, such as a lithium borate (LBO) crystal or a potassium titanyl phosphate crystal (KTP), for generating a second harmonic of the laser beam 120 emitted by the laser element 114. The laser beam 120 inside the resonator 108 bounces back and forth between the first and second resonator mirrors 110 and 112, reflects off a folding mirror 124 and propagates through the laser element 114 and nonlinear crystal 122. The laser element 114 has optical gain at a certain wavelength and this determines the wavelength of the laser beam 120 inside the resonator 108. This wavelength is also referred to as the fundamental wavelength. For the Nd:YAG laser element 114, the fundamental wavelength is 1064 nm.

A Q-switch 131 may be used in the resonator 108 to convert the laser beam 120 to a train of short pulses with high peak power. These short pulses increase the conversion efficiency of the second harmonic laser beam 102 and increase the average power of the laser beam 102 outside the resonator 108.

When the laser beam 120 inside the resonator 108 propagates through the nonlinear crystal 122 in a direction away from the folding mirror 124 and toward the second resonator mirror 112, a beam 102 of electromagnetic radiation at the second harmonic wavelength is output from the crystal 122. The second resonator mirror 112 is highly reflective at both the fundamental and second harmonic wavelengths and both beams 120 and 102 propagate back through the nonlinear crystal 122. On this second pass, more beams 102 at the second harmonic wavelength are produced. For example, the nonlinear crystal 122 can produce a laser beam 102 having a wavelength of approximately 532 nm (green) when a Nd:YAG rod is used as the laser element 114. One advantage of the 532 nm wavelength is that it is strongly absorbed by hemoglobin in blood and, therefore, is useful for cutting, vaporizing and coagulating vascular tissue.

The folding mirror 124 is highly reflective at the fundamental wavelength and is highly transmissive at the second harmonic wavelength. Thus, the laser beam 102 at the second harmonic passes through the folding mirror 124 and produces a second harmonic laser beam 102 outside the optical resonator 108. The optical fiber 104 connects to an optical coupler 126, which couples the beam 102 to the optical fiber 102. The beam 102 travels to the optical fiber 102 to a laser delivery probe 128 coupled to a distal end 130 of the optical fiber 104. In one embodiment, the probe 128 supports the optical fiber 104 and probe tip 100 during surgical laser treatments where the beam 102 is delivered to targeted tissue of a patient through the probe tip 100. In one embodiment, the probe 128 includes an endoscope or cystoscope.

Figure 2:
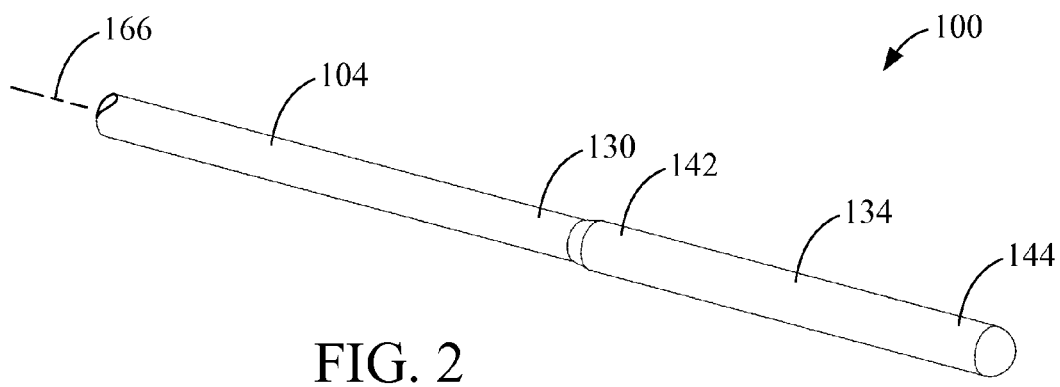
FIG. 2 is an isometric assembled view of a probe tip 100 in accordance with embodiments of the invention.
Figure 3:
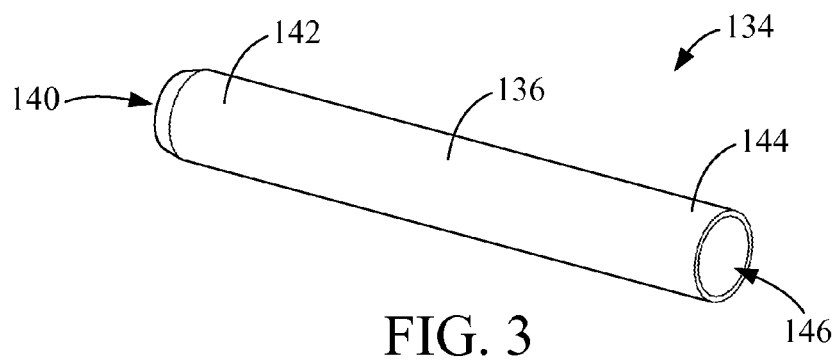
FIGS. 3 and 4 are isometric views of a fiber cap in accordance with embodiments of the invention.
Figure 4:
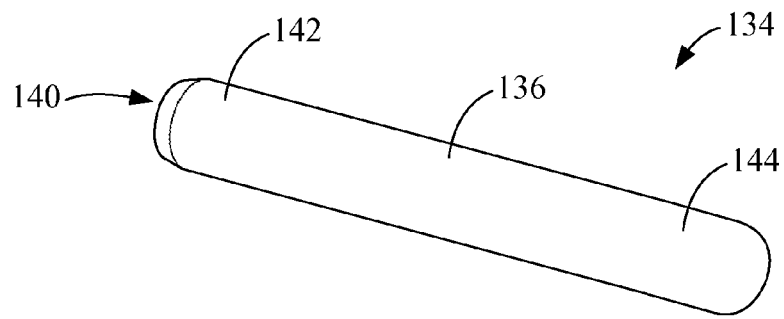

In one embodiment, the probe tip 100 comprises a fiber cap 134 attached to the distal end 130 of the optical fiber 104, as shown in the isometric assembled view provided in FIG. 2. In one embodiment, the fiber cap 134 is formed of fused silica glass. In one embodiment, the fiber cap 134 includes a cap body 136 having an interior cavity 138 and an opening 140 to the interior cavity 138 at a proximal end 142, as shown in the isometric views of FIGS. 3 and 4. In one embodiment, a distal end 144 of the fiber cap 134 has an opening 146 to the cavity 138, as shown in FIG. 3. In one embodiment, the fiber cap 134 is closed at the distal end 144, as shown in FIG. 4.

Figure 5:
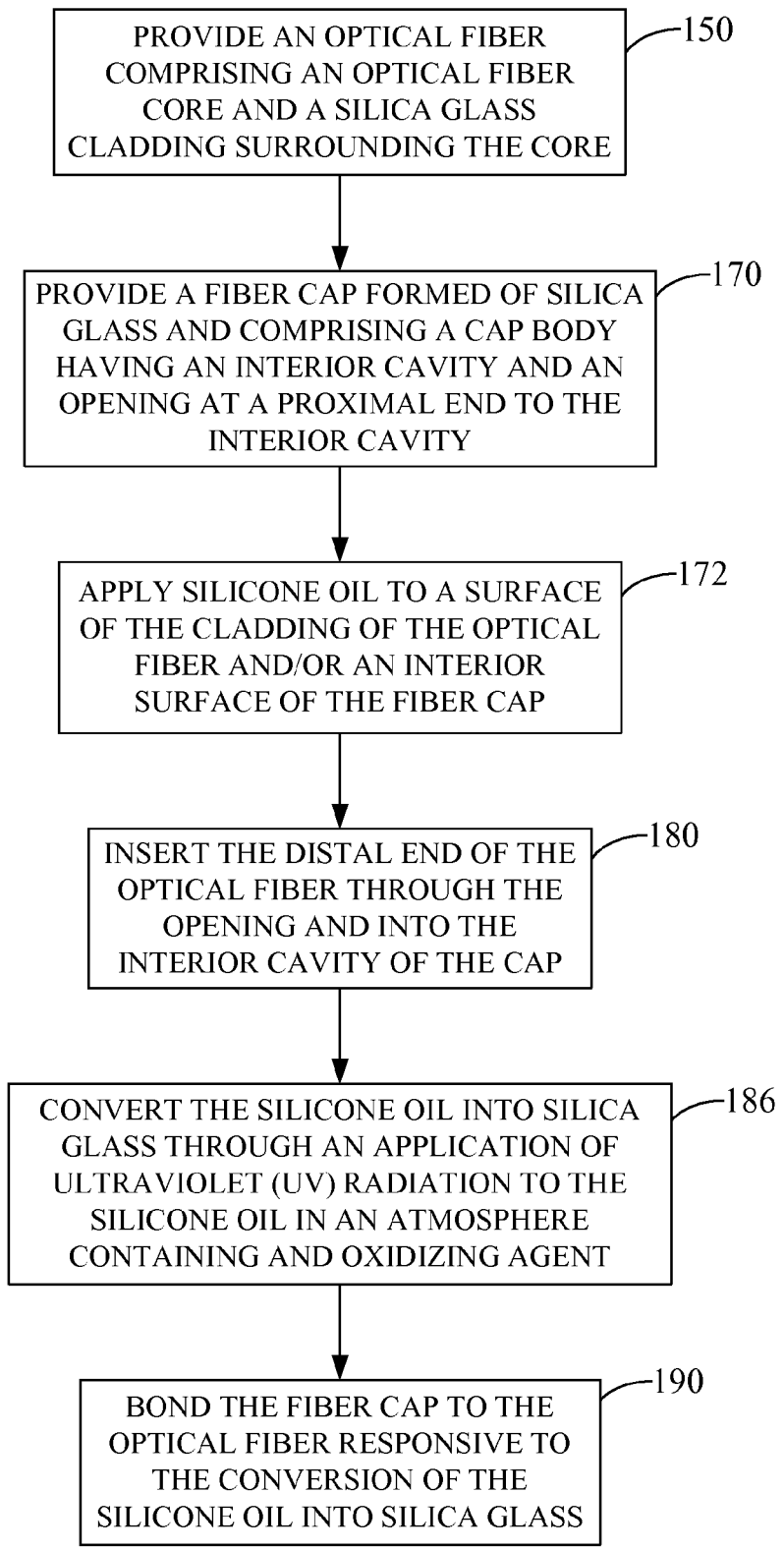
FIG. 5 is a flowchart illustrating a method of assembling a probe tip in accordance with embodiments of the invention.
Figure 8:
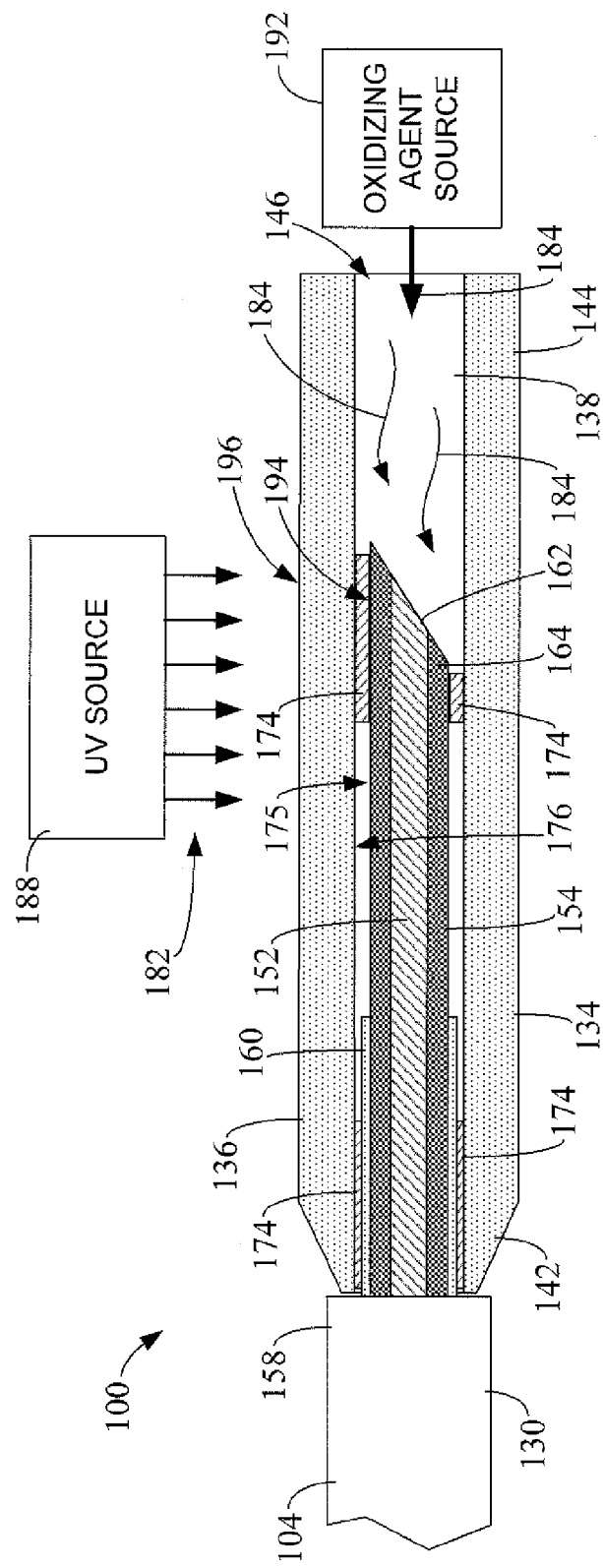
FIG. 8 is a simplified diagram illustrating one or more method steps in accordance with embodiments of the invention.
Figure 9:
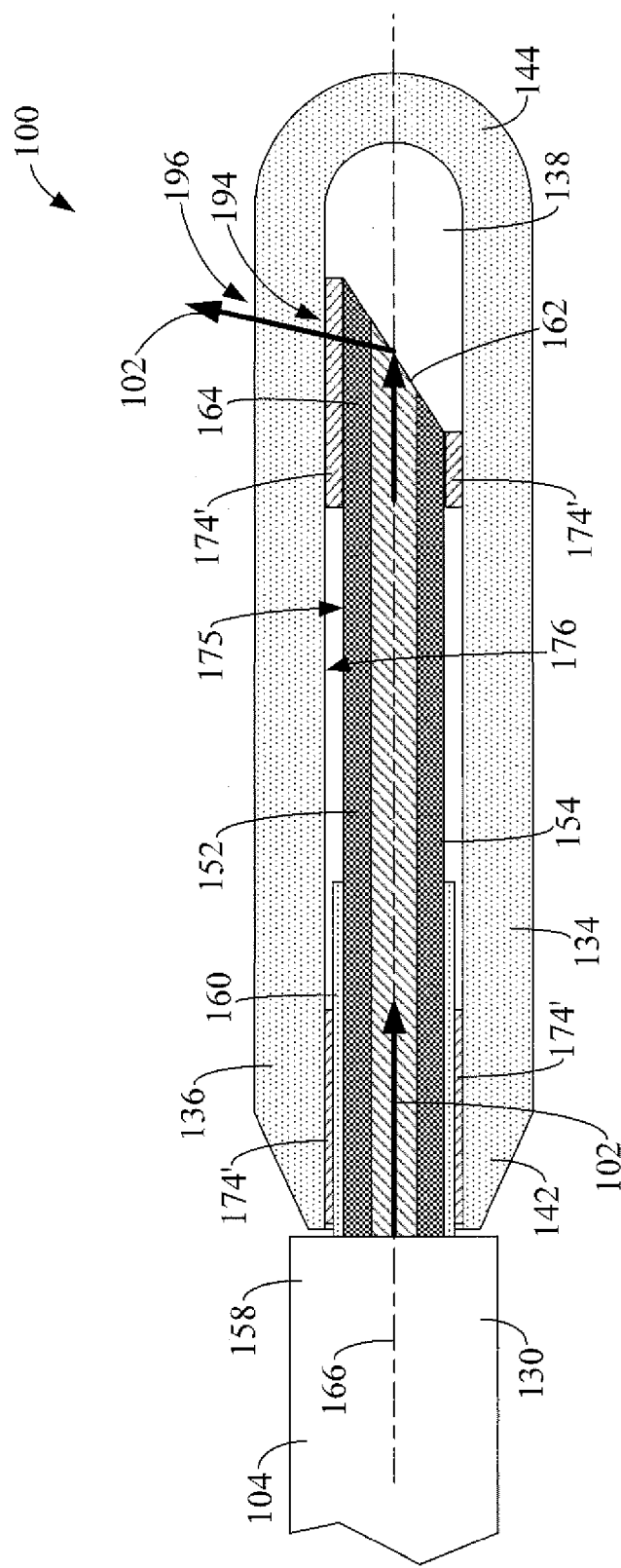
FIG. 9 is a simplified side cross-sectional view of a probe tip manufactured in accordance with embodiments of the invention.

Embodiments of the invention are directed to a method of assembling the probe tip 100. FIG. 5 is a flowchart illustrating such a method in accordance with embodiments of the invention. FIGS. 6-9 are simplified side cross-sectional views of components of the probe tip 100 at various stages of the method. More specifically, FIG. 6 is a side cross-sectional view of the distal end 130 of an exemplary optical fiber 104 at a stage of the method, FIG. 7 is a simplified side cross-sectional view of a fiber cap 134 at a stage of the method, FIG. 8 is a simplified diagram illustrating the probe tip 100 at a stage of the method and components that may be used in the method, and FIG. 9 is a simplified side cross-sectional view of the probe tip 100 manufactured in accordance with embodiments of the method.

At step 150 of the method, an optical fiber 104 comprising an optical fiber core 152 and a silica glass cladding 154 surrounding the core 152 is provided, as shown in FIG. 6. The optical fiber 104 may also include a nylon jacket 158 and a buffer or hard cladding 160. In one embodiment, the nylon jacket 158 and at least a portion of the hard cladding 160 is removed from the distal end 130 to expose the cladding 154, as shown in FIG. 6. In one embodiment, a polished beveled surface 162 is formed at a distal tip 164 of the optical fiber core 152 in accordance with conventional techniques. In one embodiment, the polished beveled surface 162 is non-perpendicular to a longitudinal axis 166 of the optical fiber core 152. Such a beveled surface 162 operates to reflect the electromagnetic energy 102 laterally from the distal tip 164, as will be discussed below. It should be understood that the distal tip 164 can take on other conventional configurations to direct the output of the electromagnetic energy 102 in a desired direction or pattern.

At step 170 of the method, a fiber cap 134 formed of silica glass is provided. As mentioned above, the fiber cap 134 comprises a cap body 136 having an interior cavity 138 and an opening 140 at a proximal end 142 to an interior cavity 138, as shown in the simplified side cross-sectional view of FIG. 7. Additionally, the distal end 144 of the fiber cap 134 may have an opening 146, as shown in FIG. 7. Alternatively, the distal end 144 of the fiber cap 134 may be closed, as shown in FIG. 4.

At step 172 of the method, silicone oil (dimethyl siloxane) is applied to a surface 175 of the cladding 154 and/or an interior surface 176 of the fiber cap 134. The silicone oil 174 can be applied to the surface 175 of the cladding 154 and/or the surface 176 of the cap body 136 using various techniques, such as dipping the components in the silicone oil, injecting the silicone oil onto the surfaces, wiping the silicone oil onto the surfaces, or other suitable technique. Embodiments of the silicone oil 174 comprise an organosilicone, an organosilicone compound, and/or a silicone polymer. One exemplary silicone oil that is suitable for use as the silicone oil 174 is silicone oil KF96-10.

At step 180 of the method, the distal end 130 of the optical fiber 104 is inserted through the opening 140 and into the interior cavity 138 of the fiber cap 134, as shown in FIG. 8. In one embodiment, the inserting step 180 is performed using a conventional apparatus that assists in aligning the distal end 130 of the optical fiber 104 to the opening 140 of the fiber cap 134 and moving the fiber cap 134 relative to the optical fiber 104 to insert the distal end 130 into the cap 134.

After the fiber cap 134 is positioned over the distal end 130 of the optical fiber 104, the silicone oil 174 is converted into silica glass, at step 186, through an application of ultraviolet (UV) radiation 182 to the silicone oil 174 in an atmosphere containing an oxidizing agent, such as oxidizing agent 184. At 190, the fiber cap 134 is bonded to the optic fiber 104 responsive to the conversion of silicone oil 174 into silica glass.

In one embodiment, the UV radiation 182 is produced by a UV source 188, such as Excimer lasers including $Ar_2$, $Kr_2$, $Xe_2$, ArF, KrF. In one embodiment the UV radiation 182 comprises an X-ray, electron beam radiation, and UV fluorescent lamp. In one embodiment, the UV radiation 182 has a wavelength of less than 250 nanometers (nm). In one embodiment, the UV radiation has a wavelength of less than 200 nm.

In one embodiment, the oxidizing agent is in the form of oxygen that is absorbed on the surface 175 of the cladding 154 and/or the surface 176 of the cap body 136. In one embodiment, an oxidizing agent source 192 generates a flow of an oxidizing agent 184. Embodiments of the oxidizing agent 184 include oxygen gas, peroxide and ozone gas. In one embodiment, the oxidizing agent source 192 provides a flow of the oxidizing agent 184 adjacent the silicone oil 174 during the converting step 186. In one embodiment, the flow of the oxidizing agent 184 is directed into the interior cavity 138, such as through the opening 146 at the distal end 144 of the fiber cap 134, as shown in FIG. 8. Alternatively, the flow of the oxidizing agent 184 can be injected into the cavity 138 using an appropriate needle or other suitable technique, particularly when the distal end 144 is closed.

During the converting step 186, the photon energy of the $Xe_2$ of lamp, which is approximately 165 kcal/mol, disassociates the Si—C bond of silicone oil because of the lower bonding energy of Si—C (105 kcal/mol). The oxidizing agent 184, such as oxygen absorbed on the surfaces 175 and/or 176, is photo-excited by the UV radiation 182 to produce $O^{1d}$, as shown in Equation (1). This active oxygen reacts with the silicone oil 174 to be modified into silica glass $(SiO_2)_n$. The methyl group ($CH_3$) is photo-disassociated from the silicone oil and reacts with the active oxygen to form carbon dioxide ($CO_2$) or water ($H_2O$), as shown in Equation (2). The active oxygen also reacts with the silicone oil to form silica glass ($SiO_2$), as shown in Equation (2).

$$O_2 + hv \rightarrow O^{1d} (\lambda < 250 [nm]) \qquad \text{Equation (1)}$$

$$[SiO(CH_3)_2]_n + O_2 + hv \rightarrow (SiO_2)_n + CO_2 + H_2O \qquad \text{Equation (2)}$$

The carbon dioxide or water generated from the photo-disassociation of the methyl group from the silicone oil may be purged from within the cavity 138 through the opening 146 at the distal end 144 of the fiber cap 134. Alternatively, suitable pathways into the cavity 138 can be formed to purge the cavity 138 of the carbon dioxide or water, when the distal end 144 of the fiber cap 134 is closed.

The conversion of the silicone oil 174 into silica glass 174' creates a layer of silica glass that extends from the surface 175 of the cladding 154 to the surface 176 of the fiber cap 134, as shown in the simplified cross-sectional view of FIG. 9. Additionally, the silica glass 174' creates a bond between the sources 175 and 176 to attach the fiber cap 134 to the distal end 130 of the optical fiber 104 and complete the method step 190. As mentioned above, the silicone oil can also be applied to the hard cladding or buffer 160 and the conversion of the silicone oil 174 to silica glass 174' forms a bond between the hard cladding 160 and the fiber cap 134.

In one embodiment, after the fiber cap 134 has been attached to the distal end 130 of the optical fiber 104, the opening 146 at the distal end 144, if present, is fused closed using a $CO_2$ laser or other suitable technique and form the probe tip 100 shown in FIG. 9. In one embodiment, the attachment of the fiber cap 134 to the optical fiber, seals the interior cavity 138.

As mentioned above, one embodiment of the optical fiber 104 includes a polished beveled surface 162 at the distal tip 164. Electromagnetic radiation 102 delivered through the optical fiber 104 through total internal reflection through the core 152 reflects off the polished beveled surface 162 laterally relative to the longitudinal axis 166 of the core 152, as shown in FIG. 9. In one embodiment, the reflected electromagnetic energy 102 is discharged through a transmitting surface 194 of the cladding 154 and a transmitting surface 196 of the fiber cap 134, as shown in FIG. 9. In one embodiment, the silicone oil 174 is applied to the surface 175 of the cladding 154 in the method step 172 such that it covers a portion of the transmitting surface 194 of the cladding 154, as shown in FIG. 6. Alternatively, the silicone oil 174 is applied to the interior surface 176 of the fiber cap 134 in the method step 172 such that it covers the area below the transmitting surface 196. Regardless of where the silicone oil 174 is applied in step 172, the silicone oil 174 is positioned between the surfaces 194 and 196 following the insertion step 180, as shown in FIG. 8. As a result, in one embodiment, the silica glass 174' is formed between the transmitting surfaces 194 and 196 in the converting step 186, as shown in FIG. 9. Thus, in one embodiment, electromagnetic energy 102 reflected off the beveled surface 162 travels through a transmitting surface 194 of the cladding 154, through the silica glass 174' and is discharged out the transmitting surface 196 of the fiber cap 134, as shown in FIG. 9.

Although the present invention has been described with reference to preferred embodiments, workers skilled in the art will recognize that changes may be made in form and detail without departing from the spirit and scope of the invention.

What is claimed is:

1. A method comprising:
providing an optical fiber comprising a core and silica glass cladding surrounding the core;
providing a fiber cap formed of silica glass, the fiber cap comprising a cap body having an interior cavity and an opening to the internal cavity at a proximal end;
applying silicone oil to at least one of a surface of the cladding at a distal end of the optical fiber and an interior surface of the fiber cap, the silicone oil comprising a component selected from the group consisting of an organosilicone, an organosilicone compound, and a silicone polymer;
inserting the distal end of the optical fiber through the opening and into the interior cavity of the fiber cap, wherein the silicone oil engages both the cladding and the fiber cap;
converting the silicone oil into silica glass comprising applying ultraviolet (UV) radiation to the silicone oil in an atmosphere containing an oxidizing agent; and
bonding the fiber cap to the optical fiber responsive to converting the silicone oil into silica glass.

2. The method of claim 1, further comprising providing the oxidizing agent, the oxidizing agent comprising a component selected from the group consisting of oxygen gas, peroxide, and ozone gas.

3. The method of claim 2, wherein providing the oxidizing agent comprising providing a flow of the oxidizing agent adjacent the silicone oil during converting silicone oil into silica glass.

4. The method of claim 3, wherein providing a flow of the oxidizing agent gas adjacent the silicone oil comprises directing the flow of the oxidizing agent into the interior cavity of the fiber cap.

5. The method of claim 1, wherein:
the cladding at the distal end of the optical fiber comprises a transmitting surface, through which electromagnetic energy delivered through the core is discharged; and
the silicone oil covers a portion of the transmitting surface following inserting the distal end of the optical fiber through the opening and into the interior cavity of the cap.

6. The method of claim 5, wherein:
the distal end of the optical fiber comprises a beveled optical surface; and
the method further comprises:
delivering electromagnetic energy through the core;
reflecting the energy off the beveled optical surface; and
discharging the energy through the transmitting surface of the cladding, the converted silicone oil, and the fiber cap.

7. The method of claim 1, wherein:
the fiber cap includes an opening at a distal end to the interior cavity; and the method comprises closing the open distal end following bonding the fiber cap to the optical fiber.

8. The method of claim 1, wherein applying UV radiation comprises applying UV radiation having a wavelength of less than 250 nanometers.

9. The method of claim 1, wherein applying UV radiation comprises applying an x-ray, electron beam radiation.

* * * * *